US010729392B2

(12) United States Patent
Yamamoto et al.

(10) Patent No.: US 10,729,392 B2
(45) Date of Patent: Aug. 4, 2020

(54) X-RAY DETECTOR, X-RAY DETECTOR MODULE, AND X-RAY CT APPARATUS

(71) Applicant: Toshiba Medical Systems Corporation, Otawara-shi (JP)

(72) Inventors: Kuniaki Yamamoto, Yokohama (JP); Ryuichi Teramoto, Yokohama (JP); Akira Nishijima, Nasushiobara (JP); Takashi Kanemaru, Yaita (JP); Minoru Horinouchi, Otawara (JP)

(73) Assignee: CANON MEDICAL SYSTEMS CORPORATION, Otawara-shi (JP)

( * ) Notice: Subject to any disclaimer, the term of this patent is extended or adjusted under 35 U.S.C. 154(b) by 428 days.

(21) Appl. No.: 15/636,077

(22) Filed: Jun. 28, 2017

(65) Prior Publication Data

US 2018/0000433 A1   Jan. 4, 2018

(30) Foreign Application Priority Data

Jun. 30, 2016   (JP) .................................. 2016-130781

(51) Int. Cl.
*A61B 6/00*   (2006.01)
*A61B 6/03*   (2006.01)

(52) U.S. Cl.
CPC ............ *A61B 6/4208* (2013.01); *A61B 6/032* (2013.01); *A61B 6/4266* (2013.01);
(Continued)

(58) Field of Classification Search
CPC ......... A61B 6/4208; A61B 6/56; A61B 6/032; A61B 6/4435
See application file for complete search history.

(56) References Cited

U.S. PATENT DOCUMENTS 5,487,098 A * 1/1996 Dobbs .................... A61B 6/032
378/19
5,635,718 A * 6/1997 DePuydt ........... H01L 27/14634
250/370.09
(Continued)

FOREIGN PATENT DOCUMENTS

JP     S60-049479 U1    4/1985
JP     H07-322380 A     12/1995
(Continued)

OTHER PUBLICATIONS

Japanese Office Action dated Mar. 3, 2020, issued in Japanese Patent Application No. 2016-130781.

*Primary Examiner* — David P Porta
*Assistant Examiner* — Djura Malevic
(74) *Attorney, Agent, or Firm* — Oblon, McClelland, Maier & Neustadt, L.L.P.

(57) ABSTRACT

An X-ray detector according to one embodiment includes X-ray detector modules, and a frame. Each X-ray detector module has a detection surface on which detection elements configured to detect X-rays are arrayed, and a supporter configured to support the detection elements. The frame fixes positions of the X-ray detector modules in such a manner that the detection surfaces of the X-ray detector modules are aligned along a first direction. The frame is provided with a pin protruding toward the supporter, at a position to which the supporter is fixed. The supporter is provided with a hole through which and into which the pin is inserted and fitted, at a position facing the frame. A movement of the supporter in the first direction is restricted by fitting the pin provided to the frame into the hole provided to the supporter, when the supporter is attached to the frame.

17 Claims, 10 Drawing Sheets

(52) U.S. Cl.
CPC .............. *A61B 6/4435* (2013.01); *A61B 6/56* (2013.01); *A61B 6/4291* (2013.01)

(56) References Cited

U.S. PATENT DOCUMENTS

| | | | | |
|---|---|---|---|---|
| 5,786,597 A * | 7/1998 | Lingren | ................. | G01T 1/161 250/370.09 |
| 5,799,057 A * | 8/1998 | Hoffman | ................ | A61B 6/032 378/147 |
| 5,847,398 A * | 12/1998 | Shahar | ................. | G01T 1/1648 250/370.09 |
| 5,955,733 A * | 9/1999 | Orava | ............... | H01L 27/14603 250/370.08 |
| 6,163,028 A * | 12/2000 | Orava | ............... | H01L 27/14603 250/370.08 |
| 6,373,915 B1 * | 4/2002 | Fujimoto | ............. | G01N 23/046 378/195 |
| 6,396,898 B1 * | 5/2002 | Saito | ................... | G01N 23/046 378/19 |
| 6,426,992 B1 * | 7/2002 | Kohler | .................. | A61B 6/032 378/15 |
| 6,510,195 B1 * | 1/2003 | Chappo | ................ | G01T 1/2018 250/208.1 |
| 6,587,538 B2 * | 7/2003 | Igarashi | ................... | A61B 6/06 250/367 |
| 6,671,345 B2 * | 12/2003 | Vrettos | ................. | A61B 6/032 378/19 |
| 6,760,404 B2 * | 7/2004 | Saito | ................... | G01N 23/046 250/370.09 |
| 6,925,142 B2 * | 8/2005 | Pohan | .................. | A61B 6/035 250/370.15 |
| 6,982,423 B2 * | 1/2006 | Elgali | .................. | G01T 1/1648 250/370.11 |
| 7,075,089 B2 * | 7/2006 | Pohan | .................... | A61B 6/585 250/363.04 |
| 7,177,387 B2 * | 2/2007 | Yasunaga | ................ | A61B 6/032 250/370.09 |
| 7,189,971 B2 * | 3/2007 | Spartiotis | .............. | G01T 1/2928 250/370.09 |
| 7,190,759 B2 * | 3/2007 | Ratzmann | ............... | A61B 6/035 250/370.09 |
| 7,196,331 B2 * | 3/2007 | Heismann | ............... | A61B 6/032 250/367 |
| 7,223,981 B1 * | 5/2007 | Capote | ................ | H01L 27/14634 250/370.13 |
| 7,233,641 B2 * | 6/2007 | Hilderscheid | .......... | A61B 6/035 250/370.15 |
| 7,235,790 B2 * | 6/2007 | Hoge | .................... | G01T 1/1648 250/370.09 |
| 7,259,376 B2 * | 8/2007 | Pohan | .................... | G01T 1/2018 250/370.09 |
| 7,465,931 B2 * | 12/2008 | Vogtmeier | ............ | A61B 6/4233 250/370.09 |
| 7,489,516 B2 * | 2/2009 | Lacey | .................... | A61B 6/032 250/370.08 |
| 7,492,857 B2 * | 2/2009 | Yasunaga | ................ | A61B 6/032 250/370.09 |
| 7,522,699 B2 * | 4/2009 | Pohan | ...................... | G01T 7/00 378/189 |
| 7,560,702 B2 * | 7/2009 | Meirav | .................. | A61B 6/032 250/370.09 |
| 7,564,940 B2 * | 7/2009 | Mattson | ................. | A61B 6/032 250/370.09 |
| 7,582,879 B2 * | 9/2009 | Abenaim | ................ | G01T 1/2018 250/370.11 |
| 7,586,096 B2 * | 9/2009 | Astley | ..................... | G01T 1/17 250/370.15 |
| 7,626,173 B2 * | 12/2009 | Hackenschmied | ....... | G01T 7/00 250/363.08 |
| 7,627,086 B2 * | 12/2009 | Vogtmeier | ............ | G01T 1/2985 250/370.09 |
| 7,728,298 B2 * | 6/2010 | Heismann | ............ | G01N 23/046 250/361 R |
| 7,769,128 B2 * | 8/2010 | Ratzmann | .............. | A61B 6/035 250/370.09 |
| 8,306,182 B2 * | 11/2012 | Yaoi | ....................... | A61B 6/035 250/370.09 |
| 8,768,032 B2 * | 7/2014 | Basu | ..................... | G06T 11/005 250/559.05 |
| 8,829,446 B2 * | 9/2014 | Abenaim | ................ | G01T 1/2985 250/363.01 |
| 8,861,685 B2 * | 10/2014 | Pohan | .................... | A61B 6/032 378/154 |
| 9,064,611 B2 * | 6/2015 | Freund | .................. | G21K 1/025 |
| 9,140,808 B2 * | 9/2015 | Ronda | .................. | G01T 1/1644 |
| 9,322,938 B2 * | 4/2016 | Kammerer | ............ | G01T 1/2985 |
| 9,788,804 B2 * | 10/2017 | Bailey | ..................... | A61B 6/032 |
| 9,949,702 B2 * | 4/2018 | Nam | ..................... | A61B 6/4291 |
| 10,261,195 B2 * | 4/2019 | Chappo | ................. | G01T 1/17 |
| 2002/0064252 A1 * | 5/2002 | Igarashi | ................... | A61B 6/06 378/19 |
| 2002/0067796 A1 * | 6/2002 | Hoffman | ................ | A61B 6/032 378/19 |
| 2002/0163993 A1 * | 11/2002 | Hoffman | ............... | G01T 1/2985 378/19 |
| 2003/0016779 A1 * | 1/2003 | Pohan | .................... | A61B 6/035 378/19 |
| 2003/0234363 A1 * | 12/2003 | Sekine | .................. | G01T 1/2018 250/370.11 |
| 2004/0065465 A1 * | 4/2004 | Chappo | .................. | A61B 6/032 174/66 |
| 2005/0061985 A1 * | 3/2005 | Hoffman | ................ | G01T 1/166 250/370.01 |
| 2005/0167603 A1 * | 8/2005 | Hoffman | ............... | G01T 1/2018 250/370.11 |
| 2006/0076498 A1 * | 4/2006 | Hilderscheid | ......... | G01T 1/1648 250/370.09 |
| 2006/0180769 A1 * | 8/2006 | Hackenschmied | .... | A61B 6/032 250/370.09 |
| 2006/0231767 A1 * | 10/2006 | Danzer | ................. | G01T 1/2985 250/370.11 |
| 2006/0241386 A1 * | 10/2006 | Yanagita | ................ | G01T 1/249 600/415 |
| 2008/0165921 A1 * | 7/2008 | Tkaczyk | ................ | A61B 6/032 378/19 |
| 2010/0204942 A1 * | 8/2010 | Danielsson | ............ | G01T 1/242 702/85 |
| 2011/0170658 A1 * | 7/2011 | Arakita | .................. | A61B 6/032 378/8 |
| 2012/0069954 A1 * | 3/2012 | Iso | ........................... | A61B 6/03 378/7 |
| 2012/0250819 A1 * | 10/2012 | Yoshida | ................ | A61B 6/5258 378/4 |
| 2012/0307963 A1 * | 12/2012 | Watanabe | ............. | A61B 6/4291 378/7 |
| 2013/0101081 A1 * | 4/2013 | Yaoi | ................... | H01L 27/14658 378/19 |
| 2013/0251097 A1 * | 9/2013 | Zou | ....................... | A61B 6/032 378/9 |
| 2013/0266116 A1 * | 10/2013 | Abenaim | .............. | G01N 23/046 378/20 |
| 2013/0306877 A1 * | 11/2013 | Pohan | .................... | G01T 1/2985 250/394 |
| 2014/0010343 A1 * | 1/2014 | Basu | ..................... | G01T 1/2985 378/15 |
| 2014/0010426 A1 * | 1/2014 | Basu | ..................... | G06T 11/005 382/131 |
| 2014/0233690 A1 * | 8/2014 | Hashimoto | .......... | A61B 6/4266 378/4 |
| 2015/0146844 A1 * | 5/2015 | Zamyatin | ............... | A61B 6/032 378/5 |
| 2015/0178958 A1 * | 6/2015 | Zou | ....................... | G06T 11/006 378/19 |
| 2015/0192681 A1 * | 7/2015 | Cho | ....................... | G01T 1/161 250/366 |
| 2016/0170038 A1 * | 6/2016 | Yu | ........................... | G01T 1/17 250/394 |

(56) References Cited

U.S. PATENT DOCUMENTS

FOREIGN PATENT DOCUMENTS

| | | |
|---|---|---|
| JP | 2000-271114 | 10/2000 |
| JP | 2005-241451 A | 9/2005 |
| JP | 2007-3544 | 1/2007 |
| JP | 2008-161689 A | 7/2008 |
| JP | 2012-129401 A | 7/2012 |
| JP | 2012-210291 | 11/2012 |
| JP | 3185017 U | 7/2013 |

* cited by examiner

X-RAY DETECTOR, X-RAY DETECTOR MODULE, AND X-RAY CT APPARATUS

CROSS-REFERENCE TO RELATED APPLICATIONS

This application is based upon and claims the benefit of priority from Japanese Patent Application No. 2016-130781, filed on Jun. 30, 2016; the entire contents of which are incorporated herein by reference.

FIELD

Embodiments described herein relate generally to an X-ray detector, an X-ray detector module, and an X-ray CT apparatus.

BACKGROUND

Conventionally available as an X-ray detector installed in an X-ray computed-tomography (CT) apparatus is one including an arrangement of a plurality of X-ray detector modules. Each of the X-ray detector modules included in such an X-ray detector has, for example, a detection surface on which a plurality of detection elements detecting X-rays are arrayed at predetermined positions, and the X-ray detector modules are fixed to a frame with their detection surfaces aligned in a predetermined direction. With such a structure of the X-ray detector, each of the X-ray detector modules is fixed to the frame by accessing from the side of the detection surface, for example.

Generally speaking, in the X-ray detector installed in an X-ray CT apparatus, the detection surfaces of the X-ray detector modules are covered by a douser in order to suppress the light incident on the detection elements. Therefore, in a structure in which each of the X-ray detector modules are fixed by accessing from the side of the detection surface, for example, the douser needs to be removed in order to replace an X-ray detector module, which may cause the serviceability to be quite low.

DETAILED DESCRIPTION

An X-ray detector according to one embodiment includes a plurality of X-ray detector modules, and a frame. Each of the X-ray detector modules has a detection surface on which a plurality of detection elements configured to detect X-rays are arrayed, and a supporter configured to support the detection elements. The frame is configured to fix positions of the X-ray detector modules in such a manner that the detection surfaces of the respective X-ray detector modules are aligned along a first direction. The frame is provided with a pin protruding toward the supporter, at a position to which the supporter is fixed. The supporter is provided with a hole through which and into which the pin is inserted and fitted, at a position facing the frame. A movement of the supporter in the first direction is restricted by fitting the pin provided to the frame into the hole provided to the supporter, when the supporter is attached to the frame.

An X-ray detector, an X-ray detector module, and an X-ray CT apparatus according to an embodiment will now be explained in detail with reference to some drawings.

Embodiment

Figure 1:
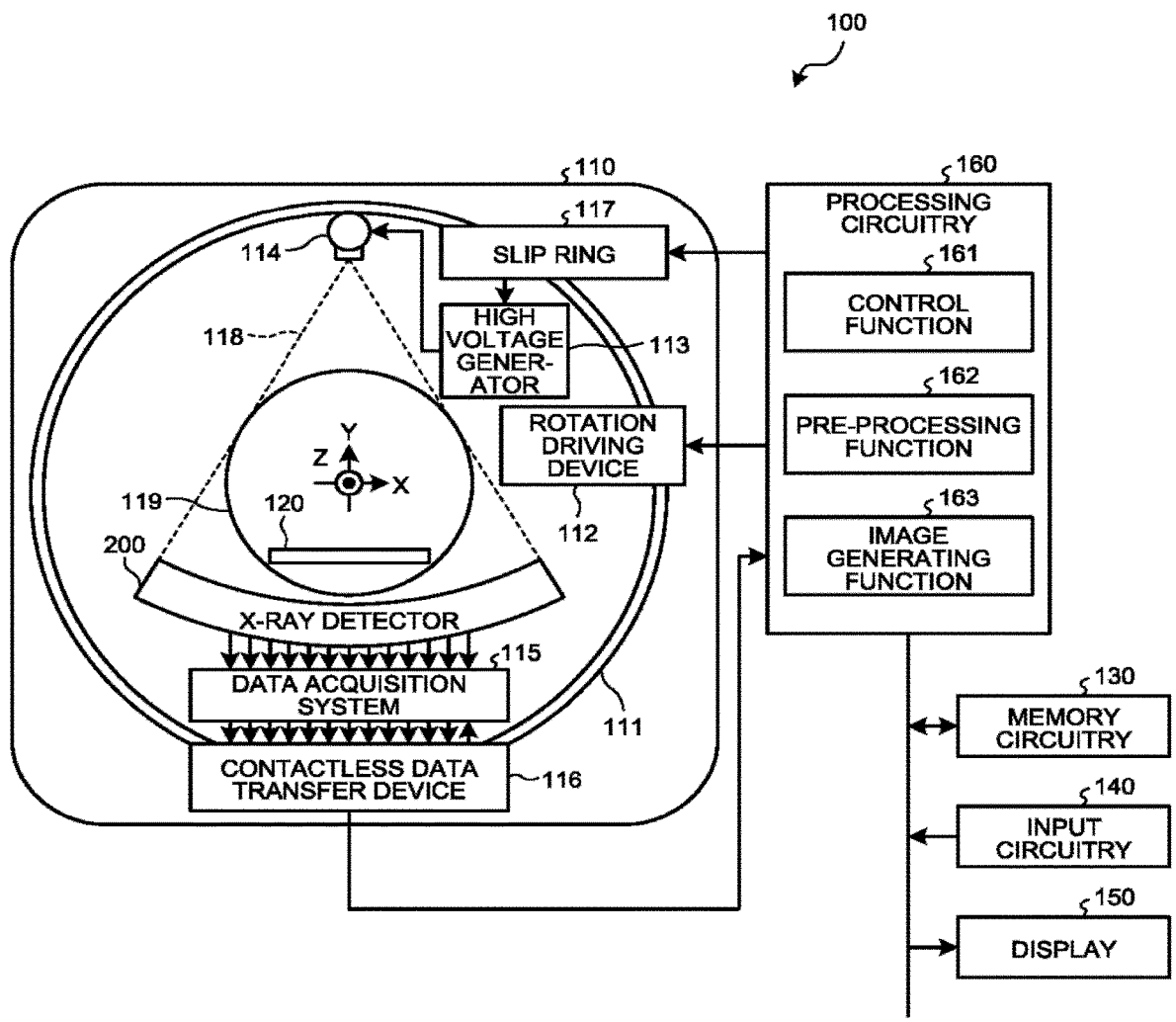
FIG. 1 is a schematic illustrating an exemplary configuration of an X-ray CT apparatus according to an embodiment.

FIG. 1 is a schematic illustrating an exemplary configuration of an X-ray CT apparatus according to an embodiment. As an example, as illustrated in FIG. 1, this X-ray CT apparatus 100 according to the embodiment includes a gantry 110, a table top 120, memory circuitry 130, input circuitry 140, a display 150, and processing circuitry 160.

The gantry 110 houses therein a rotational support mechanism that includes a rotating frame ill, a rotation driving device 112, and a frame support mechanism. Mounted on the rotating frame 111 are a high voltage generator 113, an X-ray tube 114, an X-ray detector 200, and a data acquisition system (DAS) 115, and a contactless data transfer device 116. In FIG. 1, the rotational support mechanism and the frame support mechanism are not illustrated.

The rotating frame 111 is rotatably supported by the frame support mechanism about a Z axis that is a rotational axis set to the X-ray CT apparatus 100. An apparatus coordinate system including an X axis, a Y axis, and the Z axis is set to the X-ray CT apparatus 100. The X axis is an axis in the horizontal direction that is perpendicular to the Z axis. The Y axis is an axis that is perpendicular to the X axis and the Z axis.

The rotation driving device 112 drives the rotating frame 111 in rotation. The rotation driving device 112 is implemented as an electric motor, for example.

The high voltage generator 113 generates a tube voltage to be applied to the X-ray tube 114, and a tube current to be supplied to the X-ray tube 114, using the power supplied from outside of the gantry 110 via a slip ring 117, under the control of the processing circuitry 160. It is also possible for the high voltage generator 113 to be installed outside of the gantry 110. In such a configuration, the high voltage generator 113 applies the tube voltage to the X-ray tube 114, and supplies the tube current to the X-ray tube 114, via the slip ring 117.

The X-ray tube 114 emits X-rays from an X-ray focus, using the tube voltage applied by the high voltage generator 113 and the tube current supplied by the high voltage generator 113. A plurality of collimator plates are installed in an X-ray radiation window provided in front of the X-ray tube 114, and the collimator plates collimate the X-ray emitted from the focus of the X-rays into a cone (pyramidal) beam. In FIG. 1, the range irradiated with the X-rays is indicated by dotted lines 118. As indicated by the dotted lines 118, the X-rays are emitted to the inside of an opening 119 provided near the center of the rotating frame 111 in the gantry 110, penetrate through the subject positioned inside of the opening 119, and become incident on the X-ray detector 200.

The X-ray detector 200 detects the X-rays emitted from the X-ray tube 114 and penetrated through the subject who is positioned in the opening 119. Specifically, the X-ray detector 200 is provided with a plurality of X-ray detector modules each of which has a detection surface on which a plurality of detection elements detecting X-rays are arrayed. The X-ray detector 200 then generates intensity distribution data representing a distribution of the intensities of the X-rays detected by the detection elements included in each of the X-ray detector modules, and outputs the intensity distribution data to the data acquisition system 115.

The X-ray detector 200 may be an indirect-conversion detector or a direct-conversion detector. For example, the detection element in an indirect-conversion detector includes a scintillator and a photosensor such as a photo-multiplier tube, and the X-ray photons incident on the detection element are converted into scintillator light by the scintillator, and the converted scintillator light is further converted into an electrical signal by the photosensor. The detection element in a direct-conversion detector is provided as a cadmium telluride (CdTe)-based semiconductor element, and the incident X-ray photons are converted directly into an electrical signal.

The data acquisition system 115 generates raw data by performing processes such as an amplifying process and an analog-to-digital (A/D) conversion process to the X-ray intensity distribution data received from the X-ray detector 200, and outputs the generated raw data to the contactless data transfer device 116.

The contactless data transfer device 116 outputs the raw data received from the data acquisition system 115 to the processing circuitry 160 via a contactless data transfer protocol that uses a magnetic signal or an optical signal, for example.

The subject is laid on the table top 120 that is caused to move in the X axis, the Y axis, and the Z axis by a table top driving device, which is not illustrated. The table top driving device moves the table top 120 to the inside of the opening 119 provided to the gantry 110, under the control of the processing circuitry 160.

The memory circuitry 130 stores therein various types of data. For example, the memory circuitry 130 stores therein a projection data medical image generated by the processing circuitry 160. The memory circuitry 130 is implemented as a random access memory (RAM), a semiconductor memory device such as a flash memory, a hard disk, or an optical disk, for example.

The input circuitry 140 receives various types of input operations from an operator, converts the received input operations into electrical signals, and outputs the electrical signals to the processing circuitry 160. The input circuitry 140 receives, for example, conditions such as collecting conditions for collecting projection data, reconstructing conditions for reconstructing a CT image, and image processing conditions for generating a processing image from the CT image, from the operator. The input circuitry 140 is implemented as a mouse, a keyboard, a trackball, a switch, a button, and a joystick, for example.

The display 150 outputs various types of information. The display 150 outputs a medical image generated by the processing circuitry 160, and a graphical user interface (GUI) for receiving various operations from the operator, for example. The display 150 is implemented as a liquid crystal panel or a cathode ray tube (CRT) monitor, for example.

The processing circuitry 160 controls operations of the entire X-ray CT apparatus 100 in response to an electrical signal corresponding to an input operation received from the input circuitry 140. For example, the processing circuitry 160 includes a pre-processing function 162, an image generating function 163, and a control function 161. The processing circuitry 160 is implemented as a processor, for example.

The control function 161 is to collect projection data of a subject by controlling the rotation driving device 112, the high voltage generator 113, the table top driving device, and the like, based on the collecting conditions received from the operator via the input circuitry 140.

The pre-processing function 162 generates projection data by performing a pre-process to a piece of raw data received from the contactless data transfer device 116, and stores the generated projection data in the memory circuitry 130. The pre-processing function 162 performs pre-processes such as a logarithmic transformation process, an offset correcting process, a sensitivity correcting process between channels, and a beam-hardening correction.

The image generating function 163 generates a medical image of the subject based on the X-rays detected by the X-ray detector 200, and stores the generated medical image in the memory circuitry 130.

Specifically, the image generating function 163 reconstructs a CT image of the subject by performing a reconstructing process to the projection data generated by the pre-processing function 162, based on the reconstructing conditions received from the input circuitry 140. For example, the image generating function 163 reconstructs a three-dimensional image (volume data) using the Feldkamp method or the cone-beam reconstruction method. As another example, the image generating function 163 reconstructs a two-dimensional image (tomographic image) using a back projection process such as a fan-beam reconstruction method or a filtered back projection (FBP) method.

The image generating function 163 also generates various types of processed image by performing various types of image processing to the CT image data, based on the image processing conditions received from the input circuitry 140. For example, the image generating function 163 generates a multi-planar reconstruction (MPR) image, a projection image such as a maximum-intensity projection (MIP) image, or a volume rendering image.

The control function 161, the pre-processing function 162, and the image generating function 163 provided to the processing circuitry 160 are stored as computer-executable programs in the memory circuitry 130, for example. The processing circuitry 160 is a processor for implementing the functions of the computer programs by reading the computer programs from the memory circuitry 130, and executing the computer programs. In other words, the processing circuitry 160 having read the computer programs corresponding to the respective functions have the control function 161, the pre-processing function 162, and the image generating function 163 illustrated inside of the processing circuitry 160 in FIG. 1.

Explained above is the example illustrated in FIG. 1 in which the control function 161, the pre-processing function 162, and the image generating function 163 provided to the processing circuitry 160 are implemented by one processor, but the embodiment is not limited thereto. For example, the functions provided to the processing circuitry 160 may be implemented by being distributed among or integrated into one or more processors.

The term "processor" used in the explanation above means a circuit such as a central processing unit (CPU), a graphics processing unit (GPU), an application specific integrated circuit (ASIC), or a programmable logic device (such as a simple programmable logic device (SPLD), a complex programmable logic device (CPLD), and a field programmable gate array (FPGA)). The processor implements a function by reading a computer program stored in the memory circuitry, and executing the read computer program. Instead of storing the computer program in the memory circuitry, the computer program may also be incorporated directly into the processor circuit. In such a configuration, the processor implements a function by reading a computer program incorporated in the circuit, and executing the read computer program. The processor according to the embodiment is not limited to a configuration in which one circuit is provided for one processor, and a combination of a plurality of independent circuits may be provided as one processor, and the functions may be implemented thereby.

Figure 2:
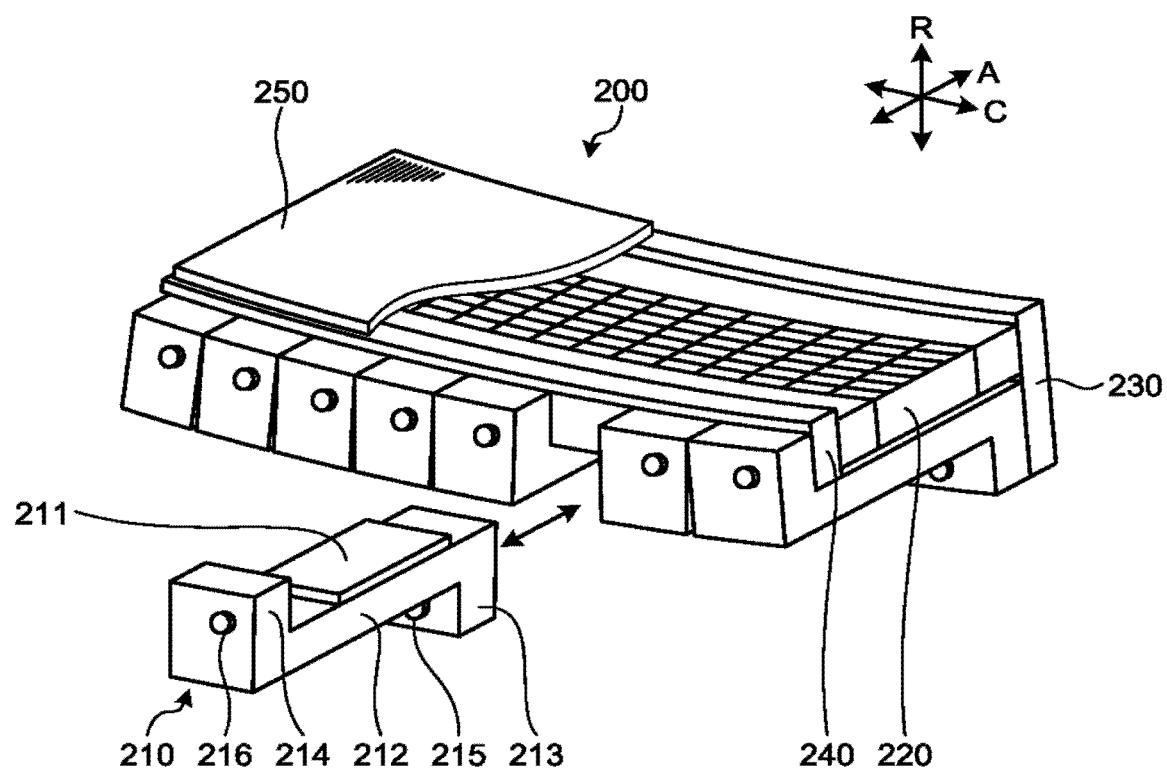
FIG. 2 is a schematic illustrating an exemplary configuration of an X-ray detector according to the embodiment.

FIG. 2 is a schematic illustrating an exemplary configuration of the X-ray detector 200 according to the embodiment. For example, as illustrated in FIG. 2, the entire X-ray detector 200 has a substantially arc shape, and is fixed to the rotating frame 111 in such a manner that the center of the arc is matched with the position of the X-ray tube 114.

In this embodiment, the radial direction of the arc of the X-ray detector 200 is referred to as a detector radial direction, and the circumferential direction is referred to as a detector circumferential direction. The direction intersecting perpendicularly with both of the detector radial direction and the detector circumferential direction is referred to as a detector axis direction. In the detector radial direction, the side closer to the center of the arc is referred to as an inner side, and the side further away from the center is referred to as an outer side. In the drawings referred in the explanation below, the detector radial direction is indicated by an arrow R, and the detector circumferential direction is indicated by an arrow C. The detector axis direction is then indicated by an arrow A. The detector axis direction is generally also referred to as a slice direction, and the detector circumferential direction is sometimes referred to as a channel direction.

Specifically, the X-ray detector 200 includes a plurality of X-ray detector modules 210, a collimator 220, a first frame 230, a second frame 240, and a douser 250.

Each of the X-ray detector modules 210 has a detection surface 211 on which a plurality of detection elements detecting X-rays are arrayed, and a supporter 212 for supporting the detection elements. For example, as illustrated in FIG. 2, the supporter 212 has a substantially cuboid shape, and supports the detection elements on its surface facing the X-ray tube 114.

The collimator 220 is a grid-like arrangement of a plurality of collimator plates, and removes scattered rays from the X-rays incident on the X-ray detector modules 210. For example, as illustrated in FIG. 2, the collimator 220 has a substantially arc shape following the detector circumferential direction, and is disposed on the incoming side of the X-ray detector modules 210 on which the X-rays are incident.

The first frame 230 and the second frame 240 fix the positions of the X-ray detector modules 210 in such a manner that the detection surfaces 211 of the respective X-ray detector modules 210 are aligned in the detector circumferential direction. For example, as illustrated in FIG. 2, the first frame 230 is fixed to one end of the collimator 220 in the detector axis direction, and the second frame 240 is fixed to the other end. The X-ray detector modules 210, aligned in the detector circumferential direction, are then attached to one side of the first frame 230 and one side of the second frame 240.

The douser 250 suppresses the light incident on the detection surface 211 of the X-ray detector modules 210. For example, as illustrated in FIG. 2, the douser 250 is a thin plate-like member that is made from a material capable of suppressing light, and is installed in a manner stretching between the first frame 230 and the second frame 240 and covering the detection surfaces 211 of the X-ray detector modules 210 aligned in the detector circumferential direction.

In the X-ray detector 200 according to the embodiment, each of the X-ray detector modules 210 is attachable or removable to or from the first frame 230 and the second frame 240 independently. Specifically, each of the X-ray detector modules 210 is independently attachable or removable by moving in the detector axis direction, while the other adjacent X-ray detector modules 210 remain attached to the frames.

With such a structure, according to this embodiment, the X-ray detector 200 has a structure capable of improving the serviceability involved in replacing the X-ray detector modules 210, as will be explained below.

In the X-ray detector 200 according to the embodiment, to begin with, the supporter 212 of the X-ray detector module 210 has two flanges protruding in the detector radial directions. The supporter 212 is configured to be attached to the frames via side surfaces of the respective flanges, using some fixers.

For example, as illustrated in FIG. 2, the supporter 212 has a first flange 213 and a second flange 214. The first flange 213 is disposed on one end of the supporter 212 in the detector axis direction, and is provided in a manner protruding toward the outer side in the detector radial direction. The second flange 214 is disposed on the other end of the supporter 212 in the detector axis direction, and is provided in a manner protruding toward the inner side in the detector radial direction.

At this time, for example, the first frame 230 has a greater width in the detector radial direction than the second frame 240 does in a manner extending toward the outer side, and the first frame 230 is configured to extend outwardly in the detector radial direction with respect to the second frame 240. The supporter 212 is then disposed in such a manner that the first flange 213 abuts against a side surface of the extending portion of the first frame 230, with the side surface being a surface facing the collimator 220, and the second flange 214 abuts against a side surface of the second frame 240, with the side surface being a surface facing the opposite side of the collimator 220. In other words, the supporter 212 is arranged in such a manner that the first and the second flanges abut against the respective side surfaces of the first and the second frames.

In such an arrangement, the supporter 212 is attached to the first frame 230 using a fixer 215 with the side surface of the first flange 213 interposed therebetween, and is attached to the second frame 240 using a fixer 216 with the side surface of the second flange 214 interposed therebetween. Examples of the fixers 215 and 216 include screws and bolts.

With the configuration described above, because the supporters 212 are attached to the frames with side surfaces of the respective flanges interposed therebetween, the X-ray detector module 210 is attachable or removable by accessing the X-ray detector module 210 from the side of the X-ray detector 200. Therefore, according to the embodiment, the X-ray detector module 210 can be replaced without removing the douser. In this manner, the serviceability involved in replacing the X-ray detector module 210 can be improved. Furthermore, the ease of assembling the X-ray detector 200 can also be improved.

Furthermore, in the X-ray detector 200 according to the embodiment, the supporter 212 of the X-ray detector module 210 is configured to be brought into sliding contact with a guide that is provided to the supporter of a counterpart X-ray detector module 210 that is adjacently positioned, so as to guide the guide in the detector axis direction.

Figure 3:
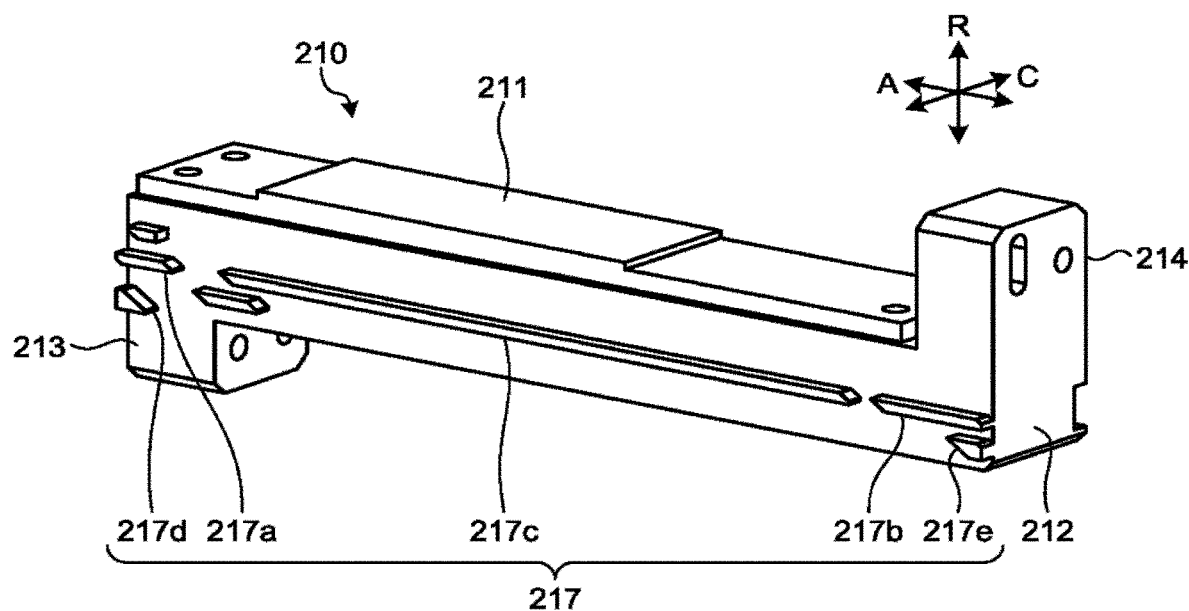
FIGS. 3 and 4 are perspective views illustrating an exemplary configuration of the X-ray detector according to the embodiment module.
Figure 4:
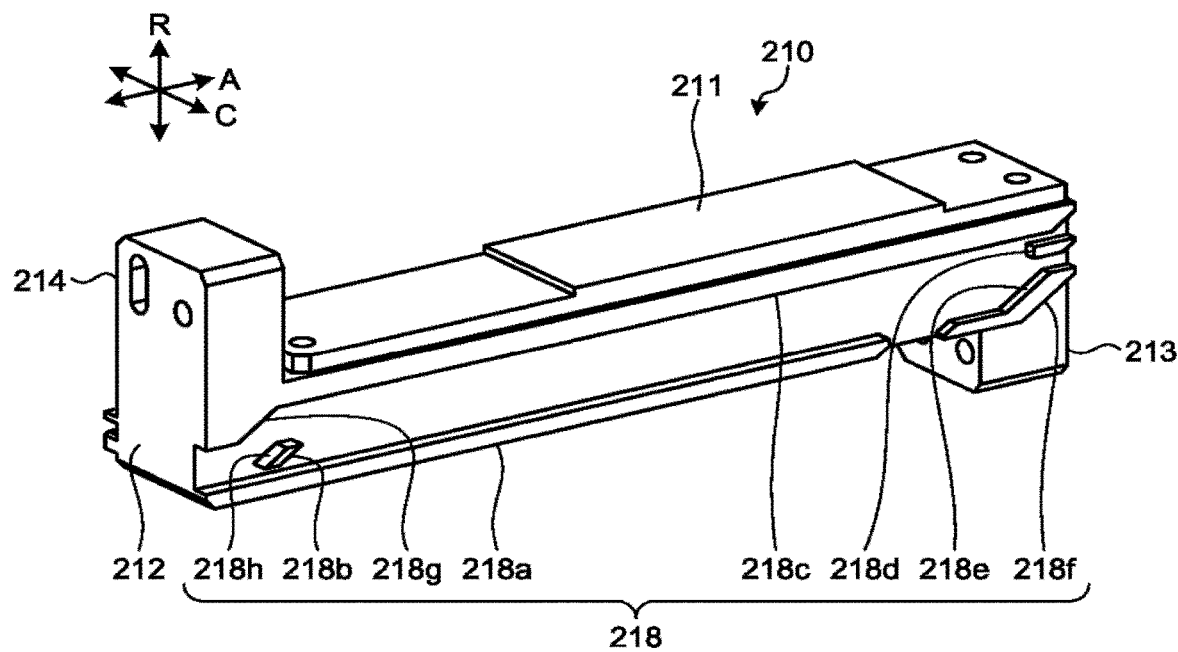

FIGS. 3 and 4 are perspective views illustrating an exemplary configuration of the X-ray detector module 210 according to the embodiment. For example, as illustrated in FIGS. 3 and 4, the supporter 212 has a first guide 217 and a second guide 218. The first guide 217 is provided on one side surface of the supporter 212 in the detector circumferential direction, and is provided protruding in the detector circumferential direction. The second guide 218 is provided on the other side surface of the supporter 212 in the detector circumferential direction, and is provided protruding in the detector circumferential direction. The second guide 218 is configured to be brought into sliding contact with the first guide 217 provided to the supporter 212 of the counterpart X-ray detector module 210 that is adjacently positioned, so as to guide the first guide 217 in the detector axis direction.

For example, as illustrated in FIG. 3, the first guide 217 has a first sliding contact portion 217a, a second sliding contact portion 217b, a third sliding contact portion 217c, a fourth sliding contact portion 217d, and a fifth sliding contact portion 217e. The structure of the first guide 217 is not limited to the example illustrated in FIG. 3, and may be changed as appropriate, correspondingly to the structure of the second guide 218, which is to be described later.

The first sliding contact portion 217a, the second sliding contact portion 217b, and the third sliding contact portion 217c all have a substantially cuboid shape extending in the detector axis direction, are arranged along the same line extending in the detector axis direction, and are arranged at the substantial center of the supporter 212 in the detector radial direction. The first sliding contact portion 217a is provided to an end of the supporter 212 on the side of the first flange 213 in the detector axis direction, and the second sliding contact portion 217b is provided to an end of the supporter 212 on the side of the second flange 214 in the detector axis direction. The third sliding contact portion 217c is positioned between the first sliding contact portion 217a and the second sliding contact portion 217b in a manner interspaced from the first sliding contact portion 217a and the second sliding contact portion 217b by predetermined distances.

The fourth sliding contact portion 217d is provided to the end of the supporter 212 on the side of the first flange 213 in the detector axis direction, and the fifth sliding contact portion 217e is provided to the end of the supporter 212 on the side of the second flange 214 in the detector axis direction. The fourth sliding contact portion 217d and the fifth sliding contact portion 217e are both positioned on the outer side with respect to the line along which the first sliding contact portion 217a, the second sliding contact portion 217b, and the third sliding contact portion 217c are aligned, in the detector radial direction.

The second guide 218 has, for example, as illustrated in FIG. 4, a first restrictor 218a, a second restrictor 218b, a third restrictor 218c, a fourth restrictor 218d, a first inclined portion 218e, a second inclined portion 218f, a third inclined portion 218g, and a fourth inclined portion 218h. The structure of the second guide 218 is not limited to the example illustrated in FIG. 4, and may be changed as appropriate, correspondingly to the structure of the first guide 217 described above.

The first restrictor 218a has a substantially cuboid shape extending in the detector axis direction, and is provided in a manner extending from the end of the supporter 212 on the side of the second flange 214 to the end on the side of the first flange 213 in the detector axis direction, along the outer end of the supporter 212 in the detector radial direction. The second restrictor 218b is provided to the end of the supporter 212 on the side of the second flange 214 in the detector axis direction, and is positioned on the inner side with respect to the first restrictor 218a in the detector radial direction.

The first restrictor 218a and the second restrictor 218b are disposed in a manner interspaced from each other in the detector radial direction by a distance that is substantially the same as the width of the first sliding contact portion 217a and the third sliding contact portion 217c in the detector radial direction. When a counterpart X-ray detector module 210 is to be attached to the first frame 230 and the second frame 240, the first sliding contact portion 217a and the third sliding contact portion 217c provided to the supporter 212 of the counterpart X-ray detector module 210 are brought into sliding contact with the first restrictor 218a and the second restrictor 218b, and thus the movement provided to the supporter 212 of the counterpart X-ray detector module 210 in the detector radial direction is restricted.

The third restrictor 218c has a substantially cuboid shape extending in the detector axis direction, and is provided in a manner extending from the end of the supporter 212 on the side of the first flange 213 to the end on the side of the second flange 214 in the detector axis direction, along the inner end of the supporter 212 in the detector radial direction. The fourth restrictor 218d is provided to the end of the supporter 212 on the side of the first flange 213 in the detector axis direction, and is positioned on the outer side with respect to the third restrictor 218c in the detector radial direction.

The third restrictor 218c and the fourth restrictor 218d are disposed in a manner interspaced from each other in the detector radial direction by a distance that is substantially the same as the width of the second sliding contact portion 217b and the third sliding contact portion 217c in the detector radial direction. When the X-ray detector module 210 is to be attached to the first frame 230 and the second frame 240, the third restrictor 218c and the fourth restrictor 218d are brought into sliding contact with the second sliding contact portion 217b and the third sliding contact portion 217c provided to the supporter 212 of a counterpart X-ray detector module 210. In this manner, the movement of the supporter 212 of the X-ray detector module 210 in the detector radial direction is restricted.

The first inclined portion 218e is provided to the end of the supporter 212 on the side of the first flange 213 in the detector axis direction, the end being an outer end in the detector radial direction. A side surface of the first inclined portion 218e includes, on the inner side in the detector radial direction, an inclined surface that is inclined to the side of the first flange 213 in the detector axis direction, from the outer side to the inner side of the supporter 212 in the detector radial direction. The inclined surface of the first inclined portion 218e is continuously provided to a range from the outer end of the supporter 212 in the detector radial direction to a position corresponding to the outer edge of the first sliding contact portion 217a.

The second inclined portion 218f is provided to the end of the supporter 212 on the side of the first flange 213 in the detector axis direction, the end being an outer end in the detector radial direction. A side surface of the second inclined portion 218f includes, on the outer side in the detector radial direction, an inclined surface that is inclined outwardly in the detector radial direction, from the side of the first flange 213 toward the side of the second flange 214 of the supporter 212 in the detector axis direction. The inclined surface of the second inclined portion 218f is continuously provided to a range overlapping with the range provided with the fourth sliding contact portion 217d, in the detector radial direction.

When a counterpart X-ray detector module 210 is to be attached to the first frame 230 and the second frame 240, the inclined surface of the first inclined portion 218e is brought into sliding contact with the first sliding contact portion 217a provided to the supporter 212 of the counterpart X-ray detector module 210, and the supporter 212 of the counterpart X-ray detector module 210 is guided in a direction approaching the detection surface 211 of the X-ray detector module 210.

When a counterpart X-ray detector module 210 is to be removed from the first frame 230 and the second frame 240, the inclined surface of the second inclined portion 218f is brought into sliding contact with the fourth sliding contact portion 217d provided to the supporter 212 of the counterpart X-ray detector module 210, and the supporter 212 of the counterpart X-ray detector module 210 is guided in a direction moving away from the detection surface 211 of the X-ray detector module 210.

The third inclined portion 218g is provided to the end of the supporter 212 on the side of the second flange 214 in the detector axis direction, the end being an inner end in the detector radial direction. A side surface of the third inclined portion 218g includes, on the outer side in the detector radial direction, an inclined surface that is inclined to the side of the second flange 214 in the detector axis direction, from the inner side toward the outer side of the supporter 212 in the detector radial direction. The inclined surface of the third inclined portion 218g is continuously provided to a range from the inner end of the supporter 212 to a position corresponding to the inner edge of the second sliding contact portion 217b in the detector radial direction.

The fourth inclined portion 218h is provided to the end of the supporter 212 on the side of the second flange 214 in the detector axis direction, the end being an outer end in the detector radial direction. A side surface of the fourth inclined portion 218h includes, on the inner side in the detector radial direction, an inclined surface that is inclined inwardly in the detector radial direction, from the side of the second flange 214 of the supporter 212 toward the side of the first flange 213 in the detector axis direction. The inclined surface of the fourth inclined portion 218h is continuously provided to a range overlapping with the range provided with the fifth sliding contact portion 217e in the detector radial direction.

When an X-ray detector module 210 is to be attached to the first frame 230 and the second frame 240, the inclined surface of the third inclined portion 218g is brought into sliding contact with the second sliding contact portion 217b provided to the supporter 212 of a counterpart X-ray detector module 210, and the supporter 212 of the X-ray detector module 210 is guided in a direction approaching the detection surface 211 of the X-ray detector module 210.

When an X-ray detector module 210 is to be removed from the first frame 230 and the second frame 240, the inclined surface of the fourth inclined portion 218h is brought into sliding contact with the fifth sliding contact portion 217e provided to the supporter 212 of a counterpart X-ray detector module 210, and the supporter 212 of the X-ray detector module 210 is guided in a direction moving away from the detection surface 211 of the X-ray detector module 210.

FIGS. 5A to 5D and 6A to 6D are schematics illustrating the processes of attaching and removing the supporter 212 according to the embodiment. Illustrated in FIGS. 5A to 5D are the first guide 217 provided to the supporter 212 that is to be attached or removed, and the second guide 218 provided to another existing supporter 212 that has been already attached and is adjacently positioned to that supporter 212. Illustrated FIGS. 6A to 6D are the second guide 218 provided to the supporter 212 that is to be attached or removed, and the first guide 217 provided to the other existing supporter 212 that has been already attached and is adjacently positioned to that supporter 212. In FIGS. 5A to 5D and 6A to 6D, the parts of the supporter 212 that is to be attached or removed are filled with a hatched pattern. In FIGS. 5A to 5D and 6A to 6D, the directions in which the supporter 212 to be attached is moved are indicated by an arrow in a solid line, and the directions in which the supporter 212 to be removed is moved are indicated by an arrow in a long dashed short dashed line.

A supporter 212 has a first section, a second section that is continuous with the first section, and a third section that is continuous with the second section. The first section is a section in which the first guide 217 provided to the supporter 212 of the counterpart X-ray detector module 210 is guided in the detector axis direction. The second section is a section in which the first guide 217 provided to the supporter 212 of the counterpart X-ray detector module 210 is guided in the detector axis direction and the detector radial direction. The third section is a section in which the first guide 217 on the supporter 212 of the counterpart X-ray detector module 210 is guided in the detector axis direction.

To begin with, explained with reference to FIGS. 5A to 5D is how the positions of the guides provided to one side surface of the supporter 212 change during the process of attaching the supporter 212.

Figure 5A:
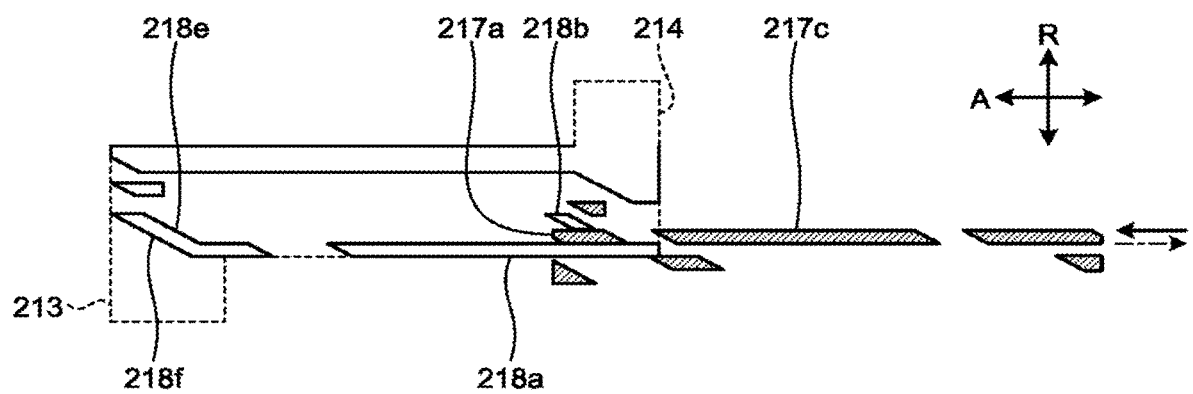
FIGS. 5A to 5D and 6A to 6D are schematics illustrating processes of attaching and removing a supporter according to the embodiment.

For example, as illustrated in FIG. 5A, when the supporter 212 is to be attached, the first sliding contact portion 217a of the supporter 212 to be attached is inserted, from the edge of on the side of the second flange 214 of the existing supporter 212, between the first restrictor 218a and the second restrictor 218b of the existing supporter 212. At this time, the supporter 212 to be attached is positioned on the outer side with respect to the existing supporter 212 in the detector radial direction.

Figure 5B:
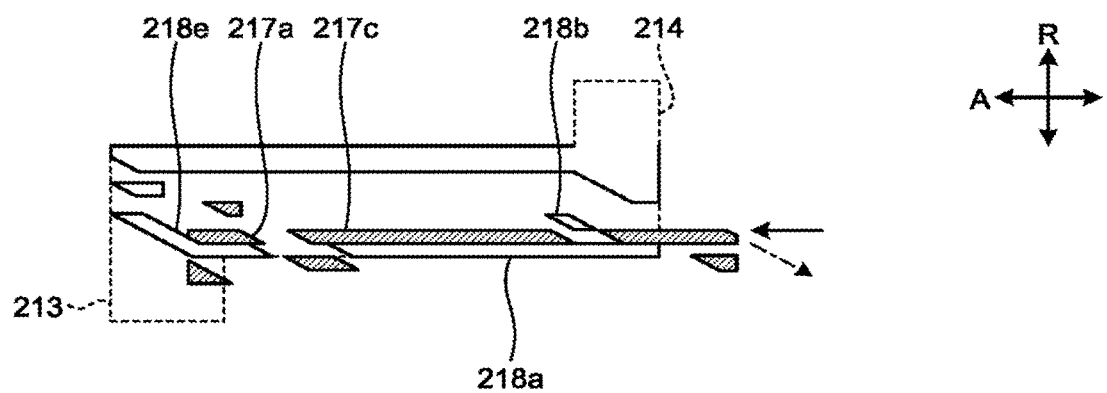

The supporter 212 to be attached is then moved in the detector axis direction, for example, as illustrated in FIG. 5B, while the movement of the supporter 212 in the detector radial direction is restricted by allowing the first sliding contact portion 217a and the third sliding contact portion 217c to be in sliding contact with the first restrictor 218a and the second restrictor 218b provided to the existing supporter 212.

Because the movement of the supporter 212 to be attached in the detector radial direction is restricted in the manner described above, shaking of the supporter 212 in the detector radial direction can be suppressed, so that the X-ray detector module 210 can be attached stably.

The supporter 212 to be attached is then moved in the detector axis direction, while the movement of the supporter 212 in the detector radial direction is restricted, until the first sliding contact portion 217a abuts against the inclined surface of the first inclined portion 218e provided to the existing supporter 212.

Figure 5C:
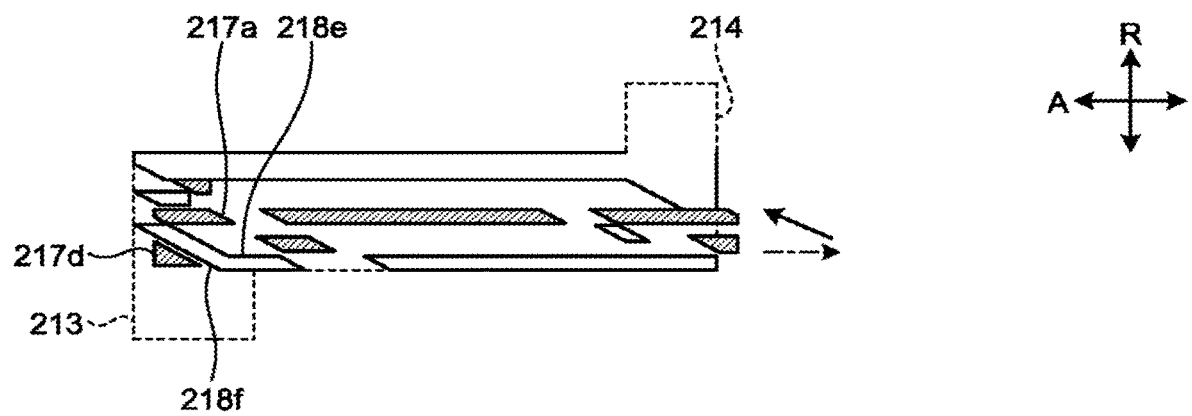

The supporter 212 to be attached is then guided in a direction approaching the detection surface 211 of the X-ray detector module 210, as illustrated in FIG. 5C, for example, while being guided in the detector axis direction, by allowing the first sliding contact portion 217a to be in sliding contact with the inclined surface of the first inclined portion 218e provided to the existing supporter 212.

In this manner, by allowing the supporter 212 to be attached to be guided in a direction approaching the detection surface 211 of the X-ray detector module 210, the X-ray detector module 210 can be attached easily.

The supporter 212 to be attached is then moved in the detector axis direction, and in a direction approaching the detection surface 211 of the existing X-ray detector module 210, until the first sliding contact portion 217a reaches the end point of the inclined surface of the first inclined portion 218e provided to the existing supporter 212. In this manner, the detection surface 211 of the supporter 212 to be attached is aligned to the same position as the detection surface 211 of the existing supporter 212 in the detector radial direction.

Figure 5D:
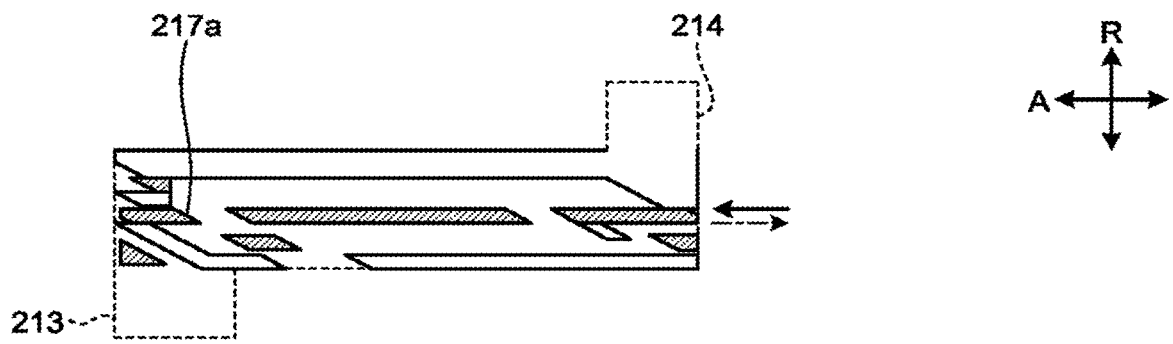

The supporter 212 to be attached is then, for example, as illustrated in FIG. 5D, further moved in the detector axis direction until the first sliding contact portion 217a reaches the edge of the existing supporter 212 on the side of the first flange 213. In this manner, attaching of the supporter 212 is completed.

In the manner described above, when the supporter 212 is to be attached, the section from the edge of the existing supporter 212 on side of the second flange 214 to the starting point of the inclined surface of the first inclined portion 218e in the existing supporter 212 serves as the first section. The section from the starting point to the end point of the inclined surface of the first inclined portion 218e in the existing supporter 212 serves as the second section. The section from the end point of the inclined surface of the first inclined portion 218e to the edge of the existing supporter 212 on the side of the first flange 213 serves as the third section.

Explained now with reference to FIGS. 5A to 5D is how the positions of the guides provided to one side surface of the supporter 212 change during the process of removing the supporter 212.

When a supporter 212 is to be removed, for example, as illustrated in FIG. 5D, the supporter 212 to be removed is moved in the detector axis direction that is reversal of the direction in which the supporter 212 is moved in the process of attaching the supporter 212, from the position where the first sliding contact portion 217a of the supporter 212 to be removed has reached the edge of the existing supporter 212 on the side of the first flange 213.

The supporter 212 to be removed is then, for example, as illustrated in FIG. 5C, further moved in the detector axis direction until the fourth sliding contact portion 217d abuts against the inclined surface of the second inclined portion 218f provided to the existing supporter 212.

The supporter 212 to be removed is then, for example, as illustrated in FIG. 5B, guided in a direction moving away from the detection surface 211 of the existing X-ray detector module 210, while being guided in the detector axis direction, by allowing the fourth sliding contact portion 217d to be in sliding contact with the inclined surface of the second inclined portion 218f provided to the existing supporter 212.

In the manner described above, because the supporter 212 to be removed is guided in a direction moving away from the detection surface 211 of the existing X-ray detector module 210, the X-ray detector module 210 can be removed easily.

The supporter 212 to be removed is then further moved in the detector axis direction and in a direction moving away from the detection surface 211 of the existing X-ray detector module 210 until the fourth sliding contact portion 217d reaches the end point of the inclined surface of the second inclined portion 218f provided to the existing supporter 212.

The supporter 212 to be removed is then, for example, as illustrated in FIG. 5A, further moved in the detector axis direction, while the movement of the supporter 212 in the detector radial direction is restricted by allowing the first sliding contact portion 217a and the third sliding contact portion 217c to be in sliding contact with the first restrictor 218a and the second restrictor 218b provided to the existing supporter 212.

In the manner described above, because the movement of the supporter 212 to be removed in the detector radial direction is restricted, shaking of the supporter 212 in the detector radial direction can be suppressed, so that the X-ray detector module 210 can be removed stably.

After the supporter 212 to be removed is further moved in the detector axis direction until the first sliding contact portion 217a reaches the edge of the existing supporter 212 on the side of the second flange 214, the supporter 212 is pulled out from the edge of the existing supporter 212 on the side of the second flange 214. In this manner, removal of the supporter 212 is completed.

In the manner described above, when the supporter 212 is to be removed, the section from the edge of the existing supporter 212 on the side of the first flange 213 to the starting point of the inclined surface of the second inclined portion 218f serves as the first section. The section from the starting point to the end point of the inclined surface of the second inclined portion 218f in the existing supporter 212 serves as the second section. The section from the end point of the inclined surface of the second inclined portion 218f to the edge of the existing supporter 212 on the side of the second flange 214 serves as the third section.

Explained now with reference to FIGS. 6A to 6D is how the positions of the guides in the other side surface of the supporter 212 change during the process of attaching the supporter 212.

Figure 6A:
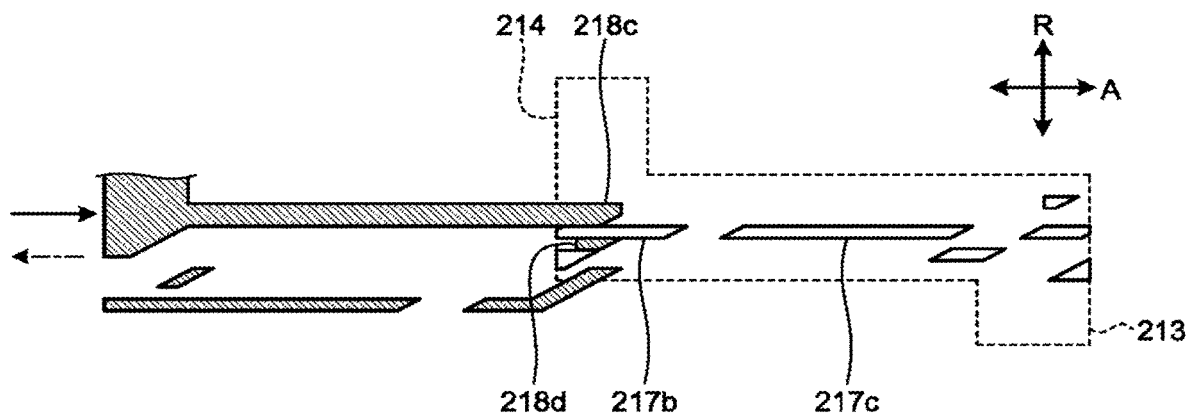

For example, as illustrated in FIG. 6A, when a supporter 212 is to be attached, the supporter 212 to be attached is inserted from the edge thereof on the side of the first flange 213, in such a manner that the second sliding contact portion 217b of the existing supporter 212 is nipped between the third restrictor 218c and the fourth restrictor 218d. At this time, the supporter 212 to be attached is positioned on the outer side with respect to the existing supporter 212 in the detector radial direction.

Figure 6B:
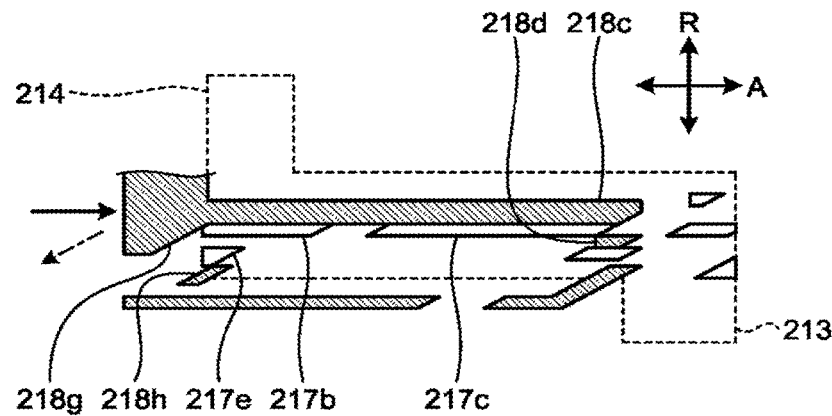

The supporter 212 to be attached is then, for example, illustrated in FIG. 6B, moved in the detector axis direction, while the movement of the supporter 212 in the detector radial direction is restricted by allowing the second sliding contact portion 217b and the third sliding contact portion 217c of the existing supporter 212 to be in sliding contact with the third restrictor 218c and the fourth restrictor 218d.

Because the movement of the supporter 212 to be attached in the detector radial direction is restricted in the manner described above, shaking of the supporter 212 in the detector radial direction can be suppressed, so that the X-ray detector module 210 can be attached stably.

The supporter 212 to be attached is then moved in the detector axis direction, while the movement of the supporter 212 in the detector radial direction is restricted, until the second sliding contact portion 217b of the existing supporter 212 abuts against the inclined surface of the third inclined portion 218g.

Figure 6C:
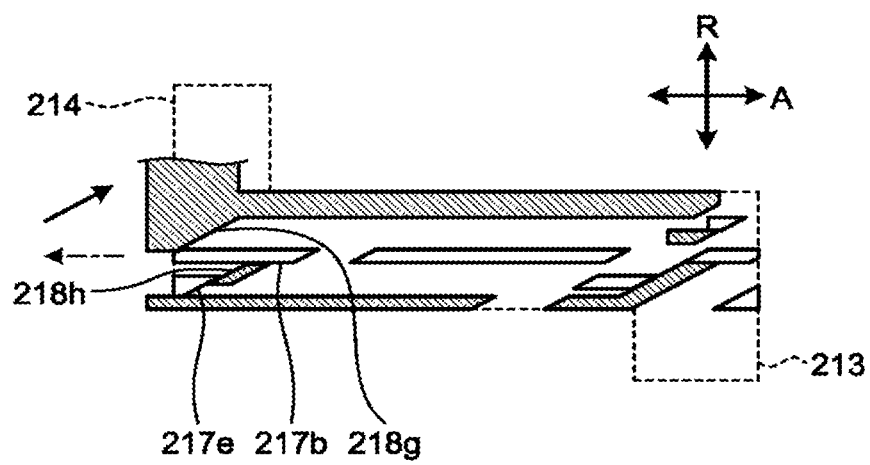

The supporter 212 to be attached is then, for example, as illustrated in FIG. 6C, guided in a direction approaching the detection surface 211 of the X-ray detector module 210, while being guided in the detector axis direction, by allowing the second sliding contact portion 217b of the existing supporter 212 to be in sliding contact with the inclined surface of the third inclined portion 218g.

In the manner described above, because the supporter 212 to be attached is guided in a direction approaching the detection surface 211 of the X-ray detector module 210, the X-ray detector module 210 can be attached more easily.

The supporter 212 to be attached is then moved in the detector axis direction, and in the direction approaching the detection surface 211 of the existing X-ray detector module 210, until the second sliding contact portion 217b of the existing supporter 212 reaches the end point of the inclined surface of the third inclined portion 218g. In this manner, the detection surface 211 of the supporter 212 to be attached is aligned to the same position as the detection surface 211 of the existing supporter 212 in the detector radial direction.

Figure 6D:
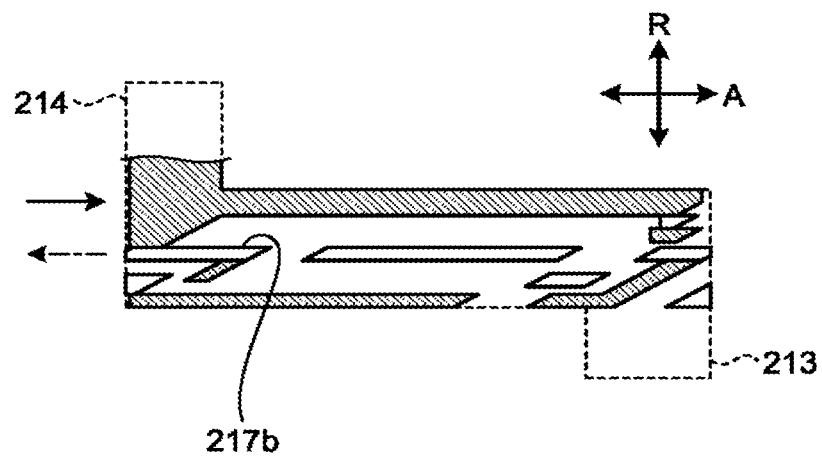

The supporter 212 to be attached is then, for example, as illustrated in FIG. 6D, further moved in the detector axis direction until the second sliding contact portion 217b of the existing supporter 212 reaches the edge of the supporter 212 to be attached on the side of the second flange 214. In this manner, attaching of the supporter 212 is completed.

In the manner described above, when the supporter 212 is to be attached, the section from the edge of the supporter 212 to be attached on the side of the first flange 213 to the starting end of the inclined surface of the third inclined portion 218g serves as the first section. The section from the starting end to the end point of the inclined surface of the third inclined portion 218g provided to the supporter 212 to be attached serves as the second section. The section from the end point of the inclined surface of the third inclined portion 218g provided to the supporter 212 to be attached to the edge on the side of the second flange 214 serves as the third section.

Explained now, also with reference to FIGS. 6A to 6D, is how the positions of the guides in the other side surface of the supporter 212 change during the process of removing the supporter 212.

When a supporter 212 is to be removed, as illustrated in FIG. 6D, for example, the supporter 212 to be removed is moved in the detector axis direction that is reversal of the direction in which the supporter 212 is moved in the process of attaching the supporter 212, from the position where the second sliding contact portion 217b of the existing supporter 212 has reached the edge of the supporter 212 to be removed, on the side of the second flange 214.

The supporter 212 to be removed is then, for example, as illustrated in FIG. 6C, further moved in the detector axis direction until the fifth sliding contact portion 217e of the existing supporter 212 abuts against the inclined surface of the fourth inclined portion 218h.

The supporter 212 to be removed is then, for example, as illustrated in FIG. 6B, is guided in a direction moving away from the detection surface 211 of the existing X-ray detector module 210, while being guided in the detector axis direction, by allowing the fifth sliding contact portion 217e of the existing supporter 212 to be in sliding contact with the inclined surface of the fourth inclined portion 218h.

In the manner described above, because the supporter 212 to be removed is guided in a direction moving away from the detection surface 211 of the existing X-ray detector module 210, the X-ray detector module 210 can be removed more easily.

The supporter 212 to be removed is then further moved in the detector axis direction and in the direction moving away from the detection surface 211 of the existing X-ray detector module 210 until the fifth sliding contact portion 217e of the existing supporter 212 reaches the end point of the inclined surface of the fourth inclined portion 218h.

The supporter 212 to be removed is then, for example, as illustrated in FIG. 6A, further moved in the detector axis direction, while the movement of the supporter 212 in the detector radial direction is restricted by allowing the second sliding contact portion 217b and the third sliding contact portion 217c of the existing supporter 212 to be in sliding contact with the third restrictor 218c and the fourth restrictor 218d.

In the manner described above, because the movement of the supporter 212 to be removed in the detector radial direction is restricted, shaking of the supporter 212 in the detector radial direction can be suppressed, so that the X-ray detector module 210 can be removed stably.

The supporter 212 to be removed is then further moved in the detector axis direction until the second sliding contact portion 217b of the existing supporter 212 reaches the edge of the first flange 213 provided to the supporter 212 to be removed, and is then pulled out from the edge of the existing supporter 212 on the side of the second flange 214. In this manner, removal of the supporter 212 is completed.

In the manner described above, when the supporter 212 is to be removed, the section from the edge of the supporter 212 to be removed on the side of the second flange 214 to the starting point of the inclined surface of the fourth inclined portion 218h serves as the first section. The section from the starting point to the end point of the inclined surface of the fourth inclined portion 218h of the supporter 212 to be removed serves as the second section. The section from the end point of the inclined surface of the fourth inclined portion 218h to the edge on the side of the first flange 213 in the supporter 212 to be removed serves as the third section.

In the manner described above, in this embodiment, because the supporter 212 is provided with the first guide 217 and the second guide 218, the movement of the X-ray detector module 210 that is to be attached or removed is guided by the existing supporter 212 that is adjacently positioned. Therefore, according to this embodiment, the X-ray detector module 210 can be replaced easily. In this manner, it is also possible to reduce the downtime.

Furthermore, the supporter 212 to be attached is guided in a direction approaching the detection surface 211 of the existing X-ray detector module 210 by the first inclined portion 218e and the third inclined portion 218g of the second guide 218, and the supporter 212 to be attached is guided in a direction moving away from the detection surface 211 of the existing X-ray detector module 210 by the second inclined portion 218*f* and the fourth inclined portion 218*h*. Therefore, the X-ray detector module 210 can be replaced regardless of the direction of the gravity working on the X-ray detector 200.

Furthermore, in the X-ray detector 200 according to the embodiment, when the supporter 212 of the X-ray detector module 210 is to be attached to the frames, a hole provided to each of the flanges is fitted with a pin provided to the frames. In this manner, the movement of the supporter 212 in the detector circumferential direction is restricted.

Specifically, pins protruding toward the first flanges 213 are provided on the first frame 230 at positions to which the respective first flanges 213 are fixed. In the same manner, pins protruding toward the second flange 214 are provided on the second frame 240 at positions to which the respective second flange 214 are fixed.

The first flange 213 is provided with a hole through which and into which a pin provided to the first frame 230 is inserted and fitted, at a position facing the first frame 230. In the same manner, the second flange 214 is provided with a hole through which and into which a pin provided to the second frame 240 is inserted and fitted, at a position facing the second frame 240.

When the supporter 212 is attached to the first frame 230, the hole provided to the first flange 213 is fitted with the corresponding pin provided to the first frame 230, and the hole provided to the second flange 214 is fitted with the corresponding pin provided to the second frame 240, and as a result, the movement of the supporter 212 in the detector circumferential direction is restricted.

As an example, the hole provided to the first frame 230 includes a first hole having a slit-shape extending in the detector radial direction, and a second hole that is connected to a part of the first hole on the side opposite to the side from which the corresponding pin is inserted, and that has a size substantially the same as the thickness of the pin. As the pin is inserted into the hole as the supporter 212 is attached to the first frame 230, the first hole is fitted with the corresponding pin, so that the movement of the supporter 212 in the detector circumferential direction is restricted, and the second hole then is fitted with the corresponding pin, so that the movements of the supporter 212 in the detector circumferential direction and the detector radial direction are restricted.

Figure 7:
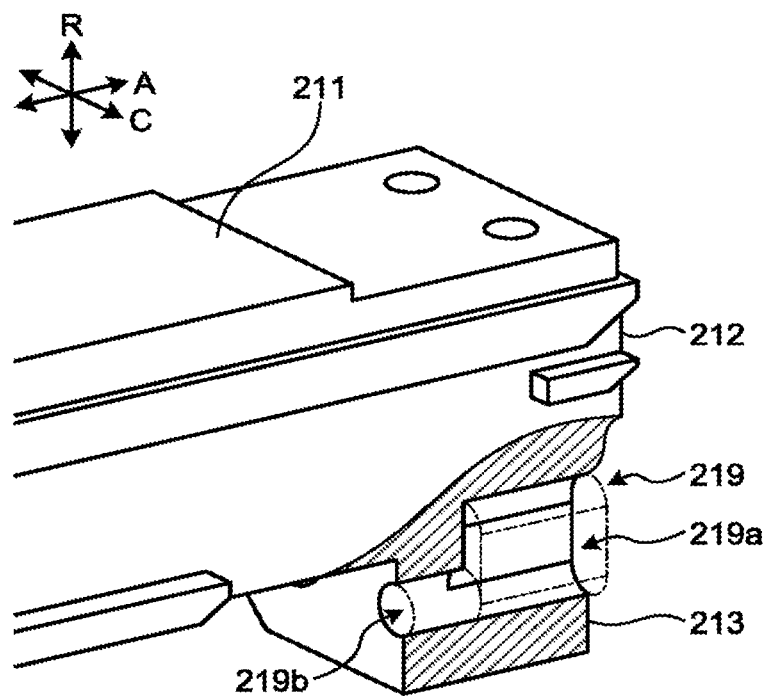
FIG. 7 is a schematic illustrating an example of a hole provided to a first flange of the supporter according to the embodiment.

FIG. 7 is a schematic illustrating an example of the hole 219 provided to the first flange 213 of the supporter 212 according to the embodiment. For example, as illustrated in FIG. 7, a hole 219 penetrating in the detector axis direction is provided to the first flange 213 at a position facing the first frame 230. The hole 219 has a shape in which a first hole 219*a* and a second hole 219*b* are connected, where first hole 219*a* is provided to the first flange 213 on the side facing the first frame 230 in the detector axis direction, and the second hole 219*b* is provided on the opposite side of such a side in the detector axis direction. The first hole 219*a* has a slit-shape extending in the detector radial direction, and the second hole 219*b* has a substantially cylindrical shape. The cylindrical second hole 219*b* is connected to the end of the slit-shaped first hole 219*a*, the end being an outer end in the detector radial direction.

The slit-shaped first hole 219*a* has a size that is substantially the same as the width of the corresponding pin provided to the first frame 230 in the detector circumferential direction. The cylindrical second hole 219*b* has a size that is substantially the same as the width of the corresponding pin provided to the first frame 230, in the detector circumferential and the detector radial directions. With such sizes, while the pin on the first frame 230 is inside of the slit-shaped first hole 219*a*, the movement of the pin in the detector circumferential direction is restricted, but the pin can move freely in the detector radial direction within the range of the first hole 219*a*. Inside of the cylindrical second hole 219*b*, by contrast, the movement of the pin on the first frame 230 in the detector circumferential direction and the detector radial direction are both restricted.

Figure 8:
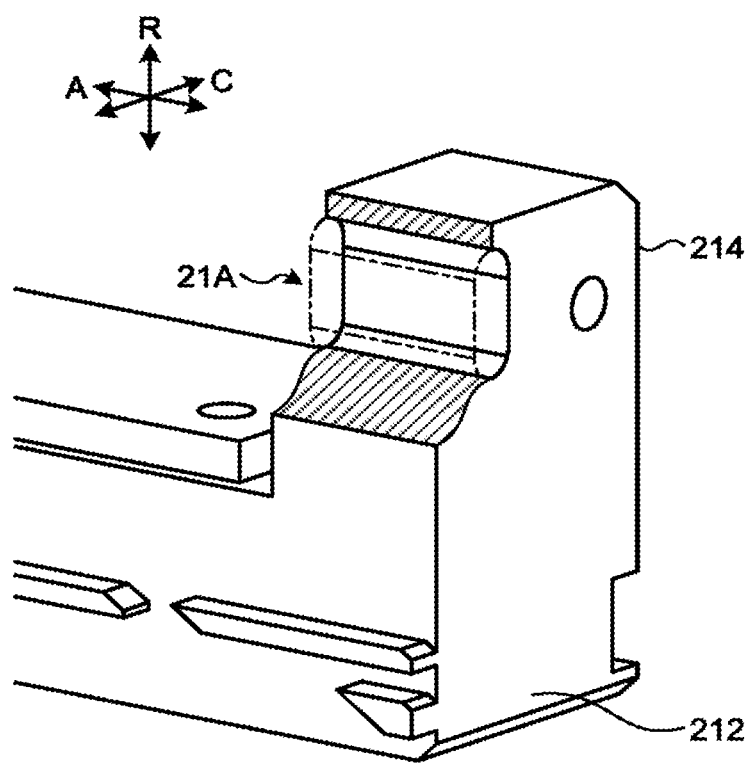
FIG. 8 is a schematic illustrating an example of a hole provided to a second flange of the supporter according to the embodiment.

FIG. 8 is a schematic illustrating an example of the hole 21A provided to the second flange 214 of the supporter 212 according to the embodiment. As an example, as illustrated in FIG. 8, a hole 21A penetrating in the detector axis direction is provided to the second flange 214 at a position facing the second frame 240. The hole 21A has a slit-shape extending in the detector radial direction, and has a size that is substantially the same as the width of the corresponding pin provided to the second frame 240, in the detector circumferential direction. In this manner, while the pin on the second frame 240 is inside of the slit-shaped hole 21A, the movement of the pin in the detector circumferential direction is restricted, but the pin can move freely in the detector radial direction within the range of the hole 21A.

Figure 9:
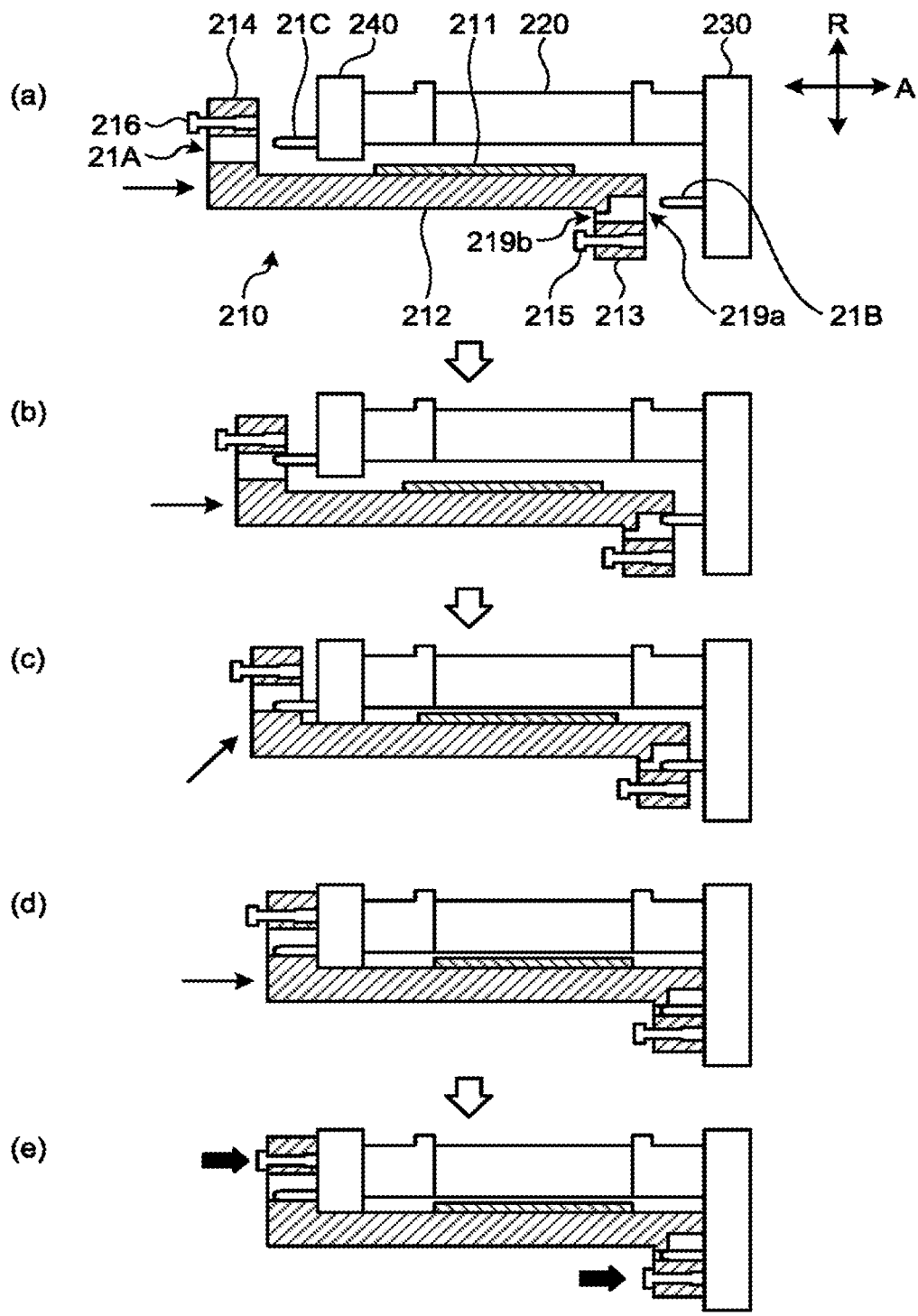
FIG. 9 is schematics illustrating how the positions of the holes on the flanges and pins on frames change during a process of attaching the supporter according to the embodiment.

FIG. 9 is a schematic illustrating how the positions of the holes on the flanges and the pins on the frames change during a process of attaching the supporter 212 according to the embodiment. For example, as illustrated in a portion (a) of FIG. 9, when the supporter 212 is to be attached, the supporter 212 to be attached is moved in the detector axis direction in an orientation in which the first flange 213 faces the first frame 230, and the second flange 214 faces the second frame 240.

The supporter 212 is then further moved, for example, in the detector axis direction, as illustrated in a portion (b) of FIG. 9, so that the pin 21B on the first frame 230 is fitted into the slit-shaped first hole 219*a* on the first flange 213, and the pin 21C on the second frame 240 is fitted into the slit-shaped hole 21A on the second flange 214.

In this configuration, the movement of the pin 21B on the first frame 230 in the detector radial direction is not restricted, but the movement in the detector circumferential direction is restricted by the slit-shaped first hole 219*a* on the first flange 213. The movement of the pin 21C on the second frame 240 in the detector radial direction is not restricted, but the movement in the detector circumferential direction is restricted. As a result, the movement of the supporter 212 in the detector radial direction is not restricted, but the movement in the detector circumferential direction is restricted.

In this manner, for example, as illustrated in a portion (c) of FIG. 9, when the supporter 212 is moved in the detector axis direction and the detector radial direction by being guided by the first guide 217 and the second guide 218, the supporter 212 can be moved stably, while the movement in the detector circumferential direction is restricted.

When the supporter 212 is further moved in the detector axis direction, for example, as illustrated in a portion (d) of FIG. 9, and the flanges abut against the respective frames, the pin 21B on the first frame 230 passes through the slit-shaped first hole 219*a* on the first flange 213, and is fitted into the cylindrical second hole 219*b*.

In this configuration, the movement of the pin 21B on the first frame 230 in both of the detector circumferential direction and the detector radial direction is restricted by the cylindrical second hole 219*b* on the first flange 213. As a result, the supporter 212 is aligned in the detector circumferential direction and the detector radial direction, while the movement in both of the detector circumferential direction and the detector radial direction is restricted.

In this manner, the supporter 212 can be attached to the frames accurately using the fixers 215 and 216, as illustrated in a portion (e) of FIG. 9, for example.

In the manner described above, according to this embodiment, when the supporter 212 is attached to the frames, the holes provided to the respective flanges become fitted with the pins provided to the respective frames, and the movement of the supporter 212 in the detector circumferential direction is restricted. Therefore, according to the embodiment, the X-ray detector module 210 can be attached stably and accurately.

As described above, according to the embodiment, the serviceability involved in replacing the X-ray detector module 210 can be improved.

Modifications

The X-ray detector module 210 explained in the embodiment described above may be implemented with some modifications as appropriate. Therefore, one of such modifications of the X-ray detector module 210 will now be explained. The supporter according to the modification described below has the same structure as that of the X-ray detector module 210 described in the embodiment unless specified otherwise.

For example, in the X-ray detector module 210 according to the embodiment described above, the supporter 212 has two flanges, but the number of flanges provided to the supporter is not limited thereto. For example, it may be sufficient if the supporter has at least one flange.

Figure 10:
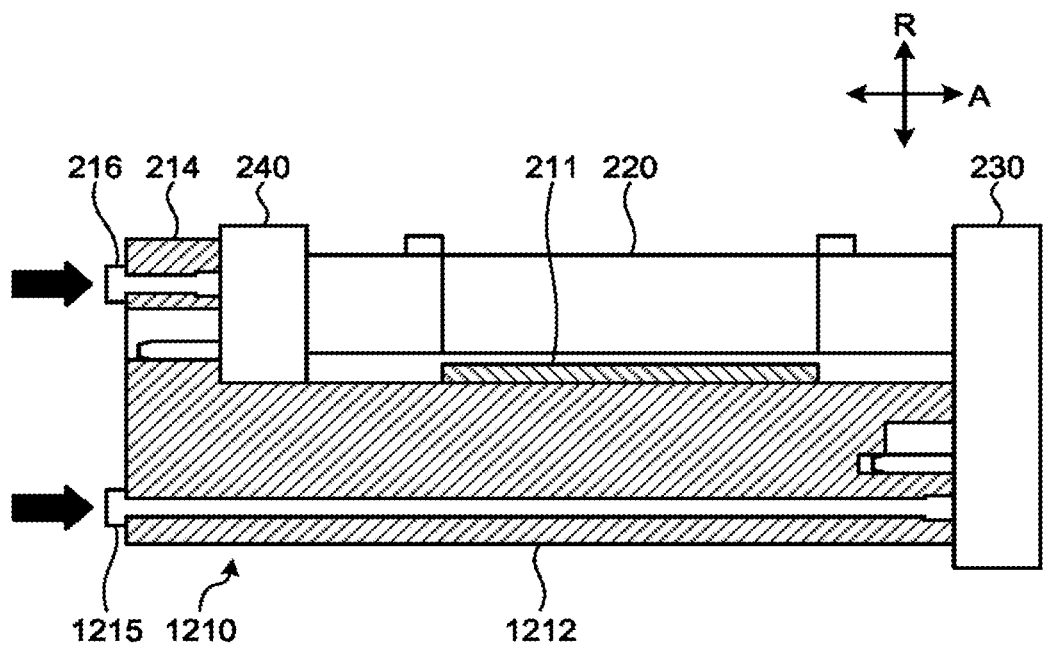
FIG. 10 is a schematic illustrating an exemplary configuration of an X-ray detector module according to a modification of the embodiment.

FIG. 10 is a schematic illustrating an exemplary configuration of an X-ray detector module 1210 according to a modification of the embodiment. As an example, as illustrated in FIG. 10, a supporter 1212 in the X-ray detector module 1210 according to the modification has only the second flange 214 explained in the embodiment. In other words, the supporter 1212 according to the modification has a structure of the supporter 212 explained in the embodiment, but without the first flange 213.

With such a structure, for example, the supporter 1212 is attached using a fixer 1215 stretching from the end provided with the second flange 214 to the first frame 230 in the detector axis direction.

Figure 11:
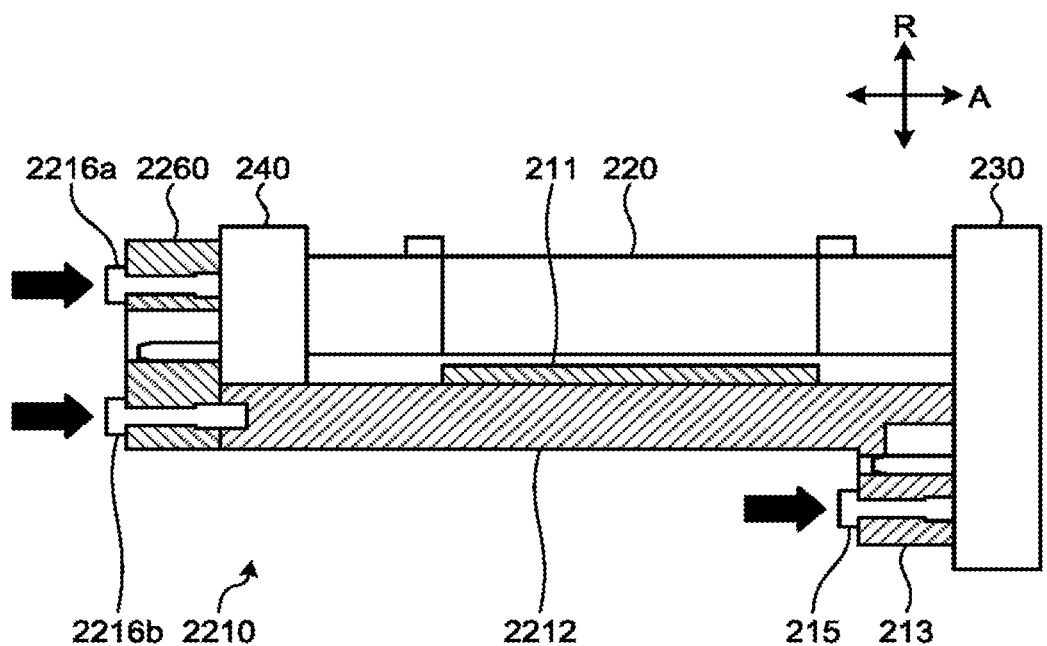
FIG. 11 is a schematic illustrating another exemplary configuration of an X-ray detector module according to a modification of the embodiment.

FIG. 11 is a schematic illustrating an exemplary configuration of an X-ray detector module 2210 according to another modification of the embodiment. As an example, as illustrated in FIG. 11, in the X-ray detector module 2210 according to the modification, a supporter 2212 only has the first flange 213 explained in the embodiment. In other words, the supporter 2212 according to the modification has the structure of the supporter 212 explained in the embodiment, but without the second flange 214.

With such a structure, for example, an end of the supporter 2212 on the opposite side of the first flange 213 in the detector axis direction is attached to the second frame 240 via a counterpart supporter 2260. In such a case, for example, the counterpart supporter 2260 is fixed to the second frame 240 with a first fixer 2216a, and is fixed to the supporter 2212 with a second fixer 2216b.

In any one of the modifications, the supporter is attached to the frame via the side surface of the flange, using a fixer. Therefore, the X-ray detector module 210 can be attached or removed by accessing from the side of the X-ray detector 200, in the same manner as in the configuration having two flanges. In this manner, according to the modifications described above, too, the X-ray detector module 210 can be replaced without removing the douser.

According to at least one of the embodiments described above, the serviceability involved in replacing the X-ray detector module 210 can be improved.

While certain embodiments have been described, these embodiments have been presented by way of example only, and are not intended to limit the scope of the inventions. Indeed, the novel embodiments described herein may be embodied in a variety of other forms; furthermore, various omissions, substitutions and changes in the form of the embodiments described herein may be made without departing from the spirit of the inventions. The accompanying claims and their equivalents are intended to cover such forms or modifications as would fall within the scope and spirit of the inventions.

What is claimed is:

1. An X-ray detector comprising:
   a plurality of X-ray detector modules each having a detection surface on which a plurality of detection elements configured to detect X-rays are arrayed, and a supporter configured to support the detection elements; and
   a frame configured to fix positions of the X-ray detector modules in such a manner that the detection surfaces of the respective X-ray detector modules are aligned along a first direction,
   wherein
   the frame is provided with a pin protruding toward the supporter, at a position to which the supporter is fixed,
   the supporter is provided with a hole through which and into which the pin is inserted and fitted, at a position facing the frame,
   a movement of the supporter in the first direction is restricted by fitting the pin provided to the frame into the hole provided to the supporter, when the supporter is attached to the frame,
   the supporter has at least one flange provided in a manner protruding in a second direction that is perpendicular to the detection surface, and
   the supporter is configured to be attached to the frame with a side surface of the at least one flange using a fixer.

2. The X-ray detector according to claim 1, wherein the supporter comprises a first guide provided on one side surface in the first direction and protruding in the first direction, and a second guide provided to another side surface in the first direction and protruding in the first direction, and
   the second guide is configured to be brought into sliding contact with the first guide provided to the supporter of a counterpart X-ray detector module that is adjacently positioned, so as to guide the first guide in a third direction that is perpendicular to both of the first direction and the second direction.

3. The X-ray detector according to claim 2, wherein the second guide comprises:
   a first inclined portion configured, when the counterpart X-ray detector module is to be attached to the frame, to be brought into sliding contact with the first guide provided to the supporter of the counterpart X-ray detector module, so as to guide the supporter of the counterpart X-ray detector module in a direction approaching the detection surface of the X-ray detector module; and
   a second inclined portion configured, when the counterpart X-ray detector module is to be removed from the frame, to be brought into sliding contact with the first guide provided to the supporter of the counterpart X-ray detector module, so as to guide the supporter of the counterpart X-ray detector module in a direction moving away from the detection surface of the X-ray detector module.

4. The X-ray detector according to claim 2, wherein the second guide comprises:
a third inclined portion configured, when the X-ray detector module is to be attached to the frame, to be brought into sliding contact with the first guide provided to the supporter of the counterpart X-ray detector module, so as to guide the supporter of the X-ray detector module in a direction approaching the detection surface of the counterpart X-ray detector module; and
a fourth inclined portion configured, when the X-ray detector module is to be removed from the frame, to be brought into sliding contact with the first guide provided to the supporter of the counterpart X-ray detector module, so as to guide the supporter of the X-ray detector module in a direction moving away from the detection surface of the counterpart X-ray detector module.

5. The X-ray detector according to claim 2, wherein
the second guide comprises a first restrictor and a second restrictor that are disposed interspaced from each other in the second direction by a distance that is substantially same as a width of the first guide, and
the first restrictor and the second restrictor are configured, when the counterpart X-ray detector module is to be attached to the frame, to restrict a movement of the supporter of the counterpart X-ray detector module in the second direction by allowing the first guide provided to the supporter of the counterpart X-ray detector module to be brought into sliding contact with the first restrictor and the second restrictor.

6. The X-ray detector according to claim 2, wherein
the second guide comprises a third restrictor and fourth restrictor that are disposed interspaced from each other in the second direction by a distance that is substantially same as a width of the first guide in the second direction, and
the third restrictor and the fourth restrictor are configured, when the X-ray detector module is to be attached to the frame, to restrict a movement of the supporter of the X-ray detector module in the second direction by allowing the first guide provided to the supporter of the counterpart X-ray detector module to be brought into sliding contact with the third restrictor and the fourth restrictor.

7. The X-ray detector according to claim 2, wherein the supporter comprises:
a first section configured to guide the first guide provided to the supporter of the counterpart X-ray detector module in the third direction;
a second section configured to be continuous with the first section, so as to guide the first guide provided to the supporter of the counterpart X-ray detector module in the third direction and in the second direction; and
a third section configured to be continuous with the second section, so as to guide the first guide provided to the supporter of the counterpart X-ray detector module in the third direction.

8. The X-ray detector according to claim 1, wherein the at least one flange is provided to at least one end of the supporter, the end being one end in a third direction that is perpendicular to both of the first direction and the second direction.

9. The X-ray detector according to claim 1, wherein the hole comprises:
a first hole having a slit-shape extending in the second direction; and
a second hole that is connected to a part of the first hole, the part being on a side opposite to a side through which and into which the pin is inserted and fitted, the second hole having a size that is substantially same as a thickness of the pin, wherein
a movement of the supporter in the first direction is restricted by the pin coming to be fitted into the first hole, and a movement of the supporter in the first direction and the second direction is restricted by the pin coming to be fitted into the second hole, as the pin is inserted into the hole when the supporter is attached to the frame.

10. An X-ray detector module comprising:
a detection surface on which a plurality of detection elements configured to detect X-rays are arrayed; and
a supporter configured to support the detection elements, wherein
a pin protruding toward the supporter is provided to a frame configured to fix a position of the X-ray detector module, at a position to which the supporter is fixed,
the supporter has a hole through which and with which the pin is inserted and fitted, at a position facing the frame,
a movement of the supporter in a first direction in which the X-ray detector module are arranged in plurality is restricted by fitting the pin provided to the frame into the hole provided to the supporter, when the supporter is attached to the frame,
the supporter has at least one flange provided in a manner protruding in a second direction that is perpendicular to the detection surface, and
the supporter is configured to be attached to the frame with a side surface of the at least one flange using a fixer.

11. The X-ray detector module according to claim 10, wherein
the supporter comprises a first guide provided on one side surface in the first direction and protruding in the first direction, and a second guide provided to another side surface in the first direction and protruding in the first direction, and
the second guide is configured to be brought into sliding contact with the first guide provided to a supporter of an adjacent X-ray detector module, so as to guide the first guide in a third direction that is perpendicular to both of the first direction and the second direction.

12. The X-ray detector module according to claim 11, wherein
the second guide comprises a first restrictor and a second restrictor that are disposed interspaced from each other in the second direction by a distance that is substantially same as a width of the first guide, and
the first restrictor and the second restrictor are configured, when the adjacent X-ray detector module is to be attached to the frame, to restrict a movement of the supporter of the adjacent X-ray detector module in the second direction by allowing the first guide provided to the supporter of the adjacent X-ray detector module to be brought into sliding contact with the first restrictor and the second restrictor.

13. The X-ray detector module according to claim 10, wherein the at least one flange is provided to at least one end of the supporter, the end being one end in a third direction that is perpendicular to both of the first direction and the second direction.

14. An X-ray CT apparatus comprising:
an X-ray tube configured to emit an X-ray; and
a detector configured to detect an X-ray emitted from the X-ray tube and penetrated through a subject, wherein the detector comprises:
 a plurality of X-ray detector modules each having a detection surface on which a plurality of detection elements configured to detect X-rays are arrayed, and a supporter configured to support the detection elements; and
 a frame configured to fix positions of the X-ray detector modules in such a manner that the detection surfaces of the respective X-ray detector modules are aligned along a first direction,
wherein
the frame is provided with a pin protruding toward the supporter, at a position to which the supporter is fixed,
the supporter is provided with a hole through which and into which the pin is inserted and fitted, at a position facing the frame,
a movement of the supporter in the first direction is restricted by fitting the pin provided to the frame into the hole provided to the supporter, when the supporter is attached to the frame,
the supporter has at least one flange provided in a manner protruding in a second direction that is perpendicular to the detection surface, and
the supporter is configured to be attached to the frame with a side surface of the at least one flange using a fixer.

15. The X-ray CT apparatus according to claim 14, wherein
the supporter comprises a first guide provided on one side surface in the first direction and protruding in the first direction, and a second guide provided to another side surface in the first direction and protruding in the first direction, and
the second guide is configured to be brought into sliding contact with the first guide provided to a supporter of an adjacent X-ray detector module, so as to guide the first guide in a third direction that is perpendicular to both of the first direction and the second direction.

16. The X-ray CT apparatus according to claim 15, wherein
the second guide comprises a first restrictor and a second restrictor that are disposed interspaced from each other in the second direction by a distance that is substantially same as a width of the first guide, and
the first restrictor and the second restrictor are configured, when the adjacent X-ray detector module is to be attached to the frame, to restrict a movement of the supporter of the adjacent X-ray detector module in the second direction by allowing the first guide provided to the supporter of the adjacent X-ray detector module to be brought into sliding contact with the first restrictor and the second restrictor.

17. The X-ray CT apparatus according to claim 14, wherein the at least one flange is provided to at least one end of the supporter, the end being one end in a third direction that is perpendicular to both of the first direction and the second direction.

\* \* \* \* \*